United States Patent
Shirai

(10) Patent No.: US 8,957,286 B2
(45) Date of Patent: Feb. 17, 2015

(54) PLANT CAPABLE OF BEARING SEEDLESS FRUITS AND METHOD OF PRODUCING VARIETY BEARING SEEDLESS FRUITS

(75) Inventor: Takeshi Shirai, Moriya (JP)

(73) Assignee: Syngenta Participations AG, Basel (CH)

( * ) Notice: Subject to any disclaimer, the term of this patent is extended or adjusted under 35 U.S.C. 154(b) by 379 days.

(21) Appl. No.: 12/865,962

(22) PCT Filed: Jan. 28, 2009

(86) PCT No.: PCT/JP2009/051360
§ 371 (c)(1),
(2), (4) Date: Aug. 3, 2010

(87) PCT Pub. No.: WO2009/098983
PCT Pub. Date: Aug. 13, 2009

(65) Prior Publication Data
US 2010/0333228 A1 Dec. 30, 2010

(30) Foreign Application Priority Data
Feb. 5, 2008 (JP) ................................ 2008-025424

(51) Int. Cl.
*A01H 1/02* (2006.01)
*A01H 1/04* (2006.01)
*A01H 1/08* (2006.01)
*A01H 5/00* (2006.01)
*A01H 5/08* (2006.01)

(52) U.S. Cl.
CPC ... *A01H 1/02* (2013.01); *A01H 5/08* (2013.01)
USPC ........ 800/317.1; 800/271; 800/274; 800/299; 800/303

(58) Field of Classification Search
None
See application file for complete search history.

(56) References Cited

U.S. PATENT DOCUMENTS

2010/0227041 A1* 9/2010 Bar et al. ...................... 426/615

FOREIGN PATENT DOCUMENTS

WO    WO 00/74468       12/2000
WO    WO 2008/152134 A1  12/2008

OTHER PUBLICATIONS

Tarchoun et al. *Capsicum* and Eggplant Newsletter 18: 32-35 (1999).*
Shifriss et al. Journal for the American Society of Horticultural Science 104(1): 94-96 (1979).*
Shifriss et al. HortScience 21(6): 1458-1459 (1986).*
Saito et al. "Development of the Parthenocarpic Eggplant Cultivator Anominori." *Bulletin of the National Institute of Vegetable and Tea Science*. vol. 6. 2007. pp. 1-11—Abstract Provided.
Saito et al. "Tan'I Kekkasei Nasu Hinshu Anominor to, sono Kanzenshu Nasika o Mezasu Ikushu ni Tsuit." http://www.vegenet.jp/yasaijoho/joho/0802/joho01.html. 2009.
Saito. "Yasashii Yasai no Hanashi Dai 3 Wa Nasu no Hinshu Kairyo." *Hojo to Dojo*. vol. 38. No. 1. 2006. pp. 20-25.
Yasugi et al. "Kozatsu Ikushu, Iwanami, Seibutsugaku Jiten." $4^{th}$ *Edition*. 1997. pp. 433.
Yasugi et al. "Modoshi Kozatsu Ikushu, Iwanami Seibutsugaku Jiten." $4^{th}$ *Edition*. 1997. pp. 1406.
European Search Report for European Patent Application No. 09708741.5 dated May 4, 2011.
Charles et al., "Seedlessness in *Capsicum annuum* L. var. longum DC. (Sendt)," J. Horticultural Sci., 54(2): 159-161 (1979).
Ishikawa et al., "High β-carotene and Capsaicinoid Contents in Seedless Fruits of 'Shishitoh' Pepper," HortScience, 39(1): 153-155 (2004).
Joshi et al., "Perspectives of Bell Pepper Breeding," J. of New Seeds, 6 (2-3): 51-74 (2004).
Saito et al., "Development of the Parthenocarpic Eggplant Cultivar 'Anominori,'" Bulletin of the Nat'l Inst of Vegetable and Tea Science, vol. 6. 2007. pp. 1-11.
Saito, "Tan'i Kekkasei Nasu Hinshu 'Anominori' to, sono Kanzenshu nasika o Mezasu Ikusnu ni Tsuite." http://www.vegenet.jp/yasaijoho/joho/0802/joho01.html (2009).

* cited by examiner

*Primary Examiner* — David T Fox
(74) *Attorney, Agent, or Firm* — Myers Bigel Sibley & Sajovec, PA

(57) ABSTRACT

Provided are a plant capable of bearing seedless fruits stably over several generations, a seedless fruit generated from this plant, a method of producing a variety capable of readily and reliably bearing seedless fruits, a variety produced by this production method, and a seedless fruit generated from the thus produced variety. Particularly provided is a plant capable of bearing seedless fruits, wherein the plant is obtained by a crossing method comprising a step (a) of selecting a first filial generation plant which is capable of bearing seedless fruits as well as having a male sterile trait and a parthenocarpic trait from the group of first filial generation plants generated by crossing between a plant of a male sterile line and a plant of a parthenocarpic line, and a step (b) of crossing the thus selected first filial generation plant with a plant of a fixed line which is capable of sustaining the parthenocarpic trait and the male sterile trait of the plant, as a pollen parent, to thereby generate a progeny plant having the parthenocarpic trait and the male sterile trait.

9 Claims, No Drawings

PLANT CAPABLE OF BEARING SEEDLESS FRUITS AND METHOD OF PRODUCING VARIETY BEARING SEEDLESS FRUITS

This application is a National Stage Application of PCT/JP2009/051360, filed 28 Jan. 2009, which claims benefit of Ser. No. 2008-025424, filed 5 Feb. 2008 in Japan and which applications are incorporated herein by reference. To the extent appropriate, a claim of priority is made to each of the above disclosed applications.

TECHNICAL FIELD

The present invention relates to a plant capable of bearing seedless fruits, a seedless fruit generated from this plant, a method of producing a variety bearing seedless fruits, a variety produced by this production method, and a seedless fruit generated from a plant of the thus produced variety.

Priority is claimed on Japanese Patent Application No. 2008-25424, filed Feb. 5, 2008, the content of which is incorporated herein by reference.

BACKGROUND ART

A breeding among plants such as vegetables and fruits has been actively conducted as in the past in seeking for new varieties having better properties such as yield performance, disease resistance and market preference. Particularly in recent years, consumers tend to seek easy-to-cook foods as well as tasty and good looking foods. For example, plants such as bell pepper and chili pepper containing inedible seeds are less appealing food because bothersome work is needed to remove seeds from these fruits when cooking or eating. If seedless vegetables or such plants can be provided from the beginning, it would meet the favor of the general consumers. Work efficiency would be also expected in the food service or such industries where large amounts of foods are consumed. For this reason, lots of attempts have been made to produce varieties bearing seedless fruits.

Various methods for producing seedless fruits have been disclosed. For example, there is a method of treating a usual seed plant with a plant hormone so as to thereby produce seedless fruits. Mainly used are colchicine for watermelons and gibberellin for grapes.

On the other hand, various methods for producing a variety bearing seedless fruits have also been disclosed. For example, there is disclosed a method (1) for producing a seedless tomato, a plant bearing seedless tomatoes or capable of bearing seedless tomatoes, or a cultivation material for such a tomato plant such as seed, comprising the steps of: a. providing a first tomato plant that contains the pk, fs-complex (i.e. a first pk, fs-parent); b. providing a second tomato plant that contains the pk, fs-complex (i.e. a second pk, fs-parent); c. crossing the first and second tomato plants for the production of a cultivation material, such as seed, which contains the pk, fs-complex; d. optionally cultivating the cultivation material thus obtained into a tomato plant capable of bearing seedless tomatoes; e. optionally growing said tomato plant until it carries the seedless tomatoes, and harvesting the seedless tomatoes thus obtained (for example, see Patent Document 1). In this method, firstly, all the first filial generation plants generated by crossing a known seedless parent and a non-seedless parent are self-pollinated. Among the thus obtained second filial generation plants, seedless or functionally sterile plants are selected and each plant is self-pollinated. This process is repeated over several generations for fixation so that a line which bears seedless fruits is produced.

Patent Document 1: Published Japanese Translation No. 2003-501053 of the PCT International Publication

DISCLOSURE OF THE INVENTION

However, in the method of using a plant hormone, it is necessary to treat each individual plant with the plant hormone at respectively appropriate amounts and appropriate time, which problematically takes a lot of labor.

On the other hand, since the above-mentioned method (1) produces a line capable of bearing seedless tomatoes, the labor-consuming issue for treating each plant with a plant hormone can be solved, but the method requires a complicated manipulation including opening a closed pollen tube of the parent tomato plant, taking out pollen from the pollen tube, and applying the pollen to the pistil of the parent tomato plant, preferably by hand, so as to cause self-pollination. In addition, in order to produce a fixed line, it is necessary to keep doing the cultivation through repeating self-pollination over several generations, which takes tremendous time and labor after all.

An object of the present invention is to provide a plant capable of bearing seedless fruits stably over several generations, a seedless fruit generated from this plant, a method of producing a variety capable of readily and reliably bearing seedless fruits, a variety produced by this production method, and a seedless fruit generated from the thus produced variety.

As a result of conducting extensive studies to solve the aforementioned problems, the inventors of the present invention found that a next generation plant inheriting both phenotypes of male sterility and parthenocarpy can be obtained by crossing a first filial generation plant having a male sterile trait and a parthenocarpic trait that has been generated by crossing between a plant of a male sterile line and a plant of a parthenocarpic line, with a plant of a line which is capable of sustaining the parthenocarpic trait and the male sterile trait of the plant, as a pollen parent; and a variety bearing seedless fruits stably over several generations can be produced by backcrossing the next generation plant with a plant of the same fixed line used as the pollen parent of the plant, as a pollen parent. This has led to the completion of the present invention.

That is, the present invention provides a plant capable of bearing seedless fruits, wherein the plant is obtained by a crossing method comprising the following steps (a) and (b): a step (a) of selecting a first filial generation plant which is capable of bearing seedless fruits as well as having a male sterile trait and a parthenocarpic trait from the group of first filial generation plants generated by crossing between a plant of a male sterile line and a plant of a parthenocarpic line; and a step (b) of crossing the thus selected first filial generation plant with a plant of a fixed line which is capable of sustaining the parthenocarpic trait and the male sterile trait of the plant, as a pollen parent, to thereby generate a progeny plant having the parthenocarpic trait and the male sterile trait.

The present invention also provides a plant capable of bearing seedless fruits, wherein the plant is obtained by the crossing method further comprising repeating the following step (c) at least one time, after said step (b): a step (c) of backcrossing the thus generated progeny plant again with a plant of the fixed line used as the pollen parent in the step (b), as a pollen parent, to thereby generate a progeny plant having the parthenocarpic trait and the male sterile trait.

The present invention also provides a plant capable of bearing seedless fruits, wherein said fixed line is a line fixed through anther culture or ovule culture.

The present invention also provides a plant capable of bearing seedless fruits, wherein the plant is bell pepper.

The present invention also provides a plant capable of bearing seedless fruits, wherein said progeny plant having the parthenocarpic trait and the male sterile trait is a plant selected from the group consisting of 3 Mi 74-2 (FERM BP-10935), 3 Mi 74-4 (FERM BP-10936), and a progeny plant thereof.

The present invention also provides a plant capable of bearing seedless fruits, wherein said fixed line is Mi 74 (FERM BP-10934).

The present invention also provides a seedless fruit generated from the plant capable of bearing seedless fruits by means of fructification rather than fertilization.

The present invention also provides a method of producing a variety capable of bearing seedless fruits, wherein a plant of a male sterile variety having a parthenocarpic trait is backcrossed with a plant of a fixed line which is capable of sustaining the parthenocarpic trait and the male sterile trait of the plant, as a pollen parent.

The present invention also provides a method of producing a variety capable of bearing seedless fruits, wherein said male sterile variety having a parthenocarpic trait is obtained by a crossing method comprising the following steps (a) and (b): a step (a) of selecting a first filial generation plant which is capable of bearing seedless fruits as well as having a male sterile trait and a parthenocarpic trait from the group of first filial generation plants generated by crossing between a plant of a male sterile line and a plant of a parthenocarpic line; and a step (b) of crossing the thus selected first filial generation plant with a plant of a fixed line which is capable of sustaining the parthenocarpic trait and the male sterile trait of the plant, as a pollen parent, to thereby generate a progeny plant having the parthenocarpic trait and the male sterile trait.

The present invention also provides a method of producing a variety capable of bearing seedless fruits, wherein said male sterile variety having a parthenocarpic trait is obtained by a crossing method comprising the following steps (a) to (c) while repeating the step (c) at least one time: a step (a) of selecting a first filial generation plant which is capable of bearing seedless fruits as well as having a male sterile trait and a parthenocarpic trait from the group of first filial generation plants generated by crossing between a plant of a male sterile line and a plant of a parthenocarpic line; a step (b) of crossing the thus selected first filial generation plant with a plant of a fixed line which is capable of sustaining the parthenocarpic trait and the male sterile trait of the plant, as a pollen parent, to thereby generate a progeny plant having the parthenocarpic trait and the male sterile trait; and a step (c) of backcrossing the thus generated progeny plant again with a plant of the fixed line used as the pollen parent in the step (b), as a pollen parent, to thereby generate a progeny plant having the parthenocarpic trait and the male sterile trait.

The present invention also provides a method of producing a variety capable of bearing seedless fruits, wherein said fixed line is a line fixed through anther culture or ovule culture.

The present invention also provides a method of producing a variety capable of bearing seedless fruits, wherein said variety capable of bearing seedless fruits is bell pepper.

The present invention also provides a method of producing a variety capable of bearing seedless fruits, wherein said male sterile variety having a parthenocarpic trait is a variety selected from the group consisting of 3 Mi 74-2 (FERM BP-10935), 3 Mi 74-4 (FERM BP-10936), and a progeny plant thereof.

The present invention also provides a method of producing a variety capable of bearing seedless fruits, wherein said fixed line is Mi 74 (FERM BP-10934).

The present invention also provides a variety produced by said method of producing a variety capable of bearing seedless fruits according to any one of the above-mentioned methods.

The present invention also provides a seedless fruit generated from a plant of said variety by means of fructification rather than fertilization.

The plant capable of bearing seedless fruits of the present invention has a parthenocarpic trait, and thus can reliably and stably generate seedless fruits simply by a conventional cultivation method, which is usual except for avoiding pollination. The properties such as the quality and the yield of the thus generated seedless fruits usually become closer to those of the fruits of the fixed line used as the pollen parent in the backcrossing for the production of the plant of the present invention. Therefore, it is expected that the seedless fruits generated from the plant of the present invention are acceptable in the market and also bring a sufficient demand. Furthermore, the plant of the present invention is able to readily generate progeny plants capable of bearing seedless fruit, simply by conducting backcrossing.

According to the method of producing a variety capable of bearing seedless fruits of the present invention, a variety capable of bearing seedless fruits can also be stably and readily produced like other fixed lines, without selecting a plant which expresses the desired phenotype per each generation. That is, the production method of the present invention is very efficient as compared to conventional methods, and is also preferable from an economical perspective.

BEST MODE FOR CARRYING OUT THE INVENTION

In the present invention, the term "parthenocarpy" means a property to induce production and development of fruits without pollination nor fertilization. Usually, fruits generated through parthenocarpy are seedless. Some types of plants may be able to exhibit a parthenocarpic trait by appropriately adjusting the cultivation environment such as the atmospheric temperature and the daylight hours. That is, some types of parthenocarpy are genetically determined while other types of parthenocarpy are determined by cultivation environments. The parthenocarpy referred to as in the present invention is the genetically determined type. Plants having a genetically determined parthenocarpic trait are preferred for the case of edible cultivation plants, because they offer high reliability and reproducibility as well as enabling the reduction of the labor for managing the cultivation environment.

In the present invention, the term "male sterility" means genetically determined infertility due to impaired fertilization caused by disorders of the male reproduction factor such as pollen, and thus seed cannot be formed. The male sterility referred to as in the present invention is not specifically limited as long as the fertilization is eventually impaired, whatever the cause is, such as completely no production of pollen itself or a functional failure of pollen. Or, the cause may be any other pollen-unrelated factor. This kind of pollen-unrelated factor can be exemplified by a blockage of the pollen tube or a morphological failure of the stamen.

The plant capable of bearing seedless fruits of the present invention is obtained by a crossing method comprising: a step (a) of selecting a first filial generation plant which is capable of bearing seedless fruits as well as having a male sterile trait and a parthenocarpic trait from the group of first filial generation plants generated by crossing between a plant of a male sterile line and a plant of a parthenocarpic line; and a step (b) of crossing the first filial generation plant thus selected in the step (a) with a plant of a fixed line which is capable of sustaining the parthenocarpic trait and the male sterile trait of the plant, as a pollen parent, to thereby generate a progeny plant having the parthenocarpic trait and the male sterile trait. In the following, each step is explained.

First, in the step (a), a first filial generation plant which is capable of bearing seedless fruits as well as having a male sterile trait and a parthenocarpic trait is selected from the group of first filial generation plants generated by crossing between a plant of a male sterile line and a plant of a parthenocarpic line. Specifically, the selection of the plant having a male sterile trait and a parthenocarpic trait is carried out from the group of first filial generation plants generated by pollinating pollen of a plant of a parthenocarpic line to a plant of a male sterile line. The plant of a male sterile line used in the step (a) is not specifically limited as long as it has a male sterile trait. It is possible to employ a plant of a known male sterile line, or a plant having a male sterile trait which has been newly produced by a known method such as anther culture. Similarly, the plant of a parthenocarpic line is not specifically limited, and it is possible to employ a plant of a known parthenocarpic line, or a plant having a parthenocarpic trait which has been newly produced by a known method such as anther culture.

As the thus selected first filial generation plant has a parthenocarpic trait, it is usually capable of bearing seedless fruits. On the other hand, it is also capable of generating next generation plants when crossed with a plant of another variety. However, depending on the crossing partner, some next generation plants may fail to inherit the carefully acquired male sterile trait and parthenocarpic trait. Therefore, it can be made possible to generate a progeny plant having the parthenocarpic trait and the male sterile trait, by crossing with a plant of a fixed line which is capable of sustaining the parthenocarpic trait and the male sterile trait of the plant, as a pollen parent. Specifically, in the step (b), the first filial generation plant thus selected in the step (a) is crossed with a plant of a fixed line which is capable of sustaining the parthenocarpic trait and the male sterile trait of the plant, as a pollen parent, by which a progeny plant having the parthenocarpic trait and the male sterile trait, that is, the plant capable of bearing seedless fruits of the present invention (hereafter may be referred to as "seedless fruit-generating plant"), can be generated.

In the above, the plant of a fixed line for use as a pollen parent to be crossed with the selected first filial generation plant is not specifically limited as long as the plant is of a fixed line which can function as a pollen parent, and is capable of sustaining the parthenocarpic trait and the male sterile trait of the first filial generation plant, that is, a plant of a fixed line which can generate second filial generation plants having the parthenocarpic trait and the male sterile trait, when crossed with the first filial generation plant. This fixed line to be crossed as the pollen parent (hereafter may be referred to as "pollen parental fixed line") may be either a parthenocarpic line or a nonparthenocarpic line, although a parthenocarpic line is preferred.

The both traits of male sterility and parthenocarpy are assumed to be attributed to pluralities of genes, although the expression mechanisms of these phenotypes are not clear in detail. Accordingly, it is very difficult without a crossing manipulation to determine which plant of line is appropriate for the selected first filial generation plant to cross with, to achieve that the next generation plant can inherit both phenotypes of male sterility and parthenocarpy of the selected first filial generation plant. For this reason, it is most reliable and preferable at present to determine which fixed line is usable as the pollen parental fixed line in the step (b), by actually conducting crossing through pollination of the first filial generation plant selected in the step (a) with pollens obtained from plants of various types of fixed lines.

The thus generated progeny plant is a plant capable of bearing seedless fruits as well as being capable of stably and readily generating progeny plants having the parthenocarpic trait and the male sterile trait, by backcrossing, similarly to the first filial generation plant being a parent. Specifically, the step (c) of backcrossing the thus generated progeny plant with a plant of the pollen parental fixed line used in the step (b), as a pollen parent, is repeated at least one time, by which a progeny plant having the parthenocarpic trait and the male sterile trait can be generated. Since the repeating times of the backcrossing in the step (c) is not specifically limited, the seedless fruit-generating plant of the present invention can be stably produced over several generations like other fixed lines.

In the production of the seedless fruit-generating plant of the present invention, the reproducibility and the reliability of the outcome of the crossing can be ensured by employing a plant of a fixed line as a pollen parent. In addition, it is preferable to employ a fixed homozygous line as the pollen parental fixed line. This is because that, if the associated genes are homozygous, the phenotypes of male sterility and parthenocarpy are more likely to be expressed and the backcrossing can be expected to be more easily conducted. Such a fixed homozygous line may be a known fixed pure line, a fixed line produced by a conventional self-pollination method, or a line fixed through anther culture or ovule culture. Anther culture and ovule culture are known production methods which can readily and quickly produce various types of fixed complete homozygote lines. The pollen parental fixed line for use in the production method of the present invention is preferably the line fixed through anther culture or ovule culture.

The method of producing a variety capable of bearing seedless fruits of the present invention comprises backcrossing a plant of a male sterile variety having a parthenocarpic trait, with a plant of a fixed line which is capable of sustaining the parthenocarpic trait and the male sterile trait of the plant, as a pollen parent. Although it is necessary in usual backcrossing to select a plant having the desired phenotype from the group of generated progeny plants, almost all progeny plants are of the male sterile variety having the parthenocarpic trait according to the production method of the present invention. In this regard, as for the male sterile variety having the parthenocarpic trait in the production method of the present invention, the seedless fruit-generating plant of the present invention can be used. In addition, the fixed line which is capable of sustaining the parthenocarpic trait and the male sterile trait, for use as the pollen parent in the production method of the present invention, may be the same as the pollen parental fixed line used in the step (b).

That is, the seedless fruit-generating plant of the present invention and the variety capable of bearing seedless fruits produced by the production method of the present invention have the parthenocarpic trait, and thus are capable of reliably and efficiently generating seedless fruits through avoiding pollination. Moreover, it is also possible to generate progeny plants having the male sterile trait and the parthenocarpic trait by pollinating with pollen harvested from the plant of the pollen parental fixed line used for the production. In the present invention, the pollination method is not specifically limited and may be achieved by a conventional method, although preferred is artificial crossing with use of pollen harvested from the plant of the pollen parental fixed line so as to reliably pollinate the pollen of target.

The seedless fruit-generating plant of the present invention and the variety produced by the production method of the present invention have no big difference from other plants of the same species, except for having a male sterile trait and a parthenocarpic trait, and can be cultured by a conventional method under similar growth conditions. In order to control the pollination, it is preferable to culture them in a closed space such as a plastic greenhouse where the environment is manageable.

The quality such as the taste or the yield of the seedless fruits generated from the seedless fruit-generating plant and the like of the present invention become closer to those of the fruits of the pollen parental fixed line used in the backcrossing, as repeating the backcrossing. For this reason, the quality or the yield of the thus generated seedless fruits can be made as desired by appropriately selecting and employing a variety of the pollen parental fixed line.

The seedless fruit-generating plant of the present invention and the variety being the object of the production method of the present invention are not specifically limited as long as they are capable of bearing seed fruits, although plants capable of bearing edible fruits are preferred. They are either annuals or perennials. Such plants can be exemplified by solanaceous plants including a bell pepper, a paprika, a chili pepper, an eggplant, and a tomato. For the seedless fruit-generating plant of the present invention, preferred are a bell pepper, a paprika, and a chili pepper, and more preferred is a bell pepper.

For example, in the case of a bell pepper, firstly, a bell pepper of a known male sterile breeding line "MS Shosuke" is crossed with bell peppers of known parthenocarpic breeding lines "A3" or "A7". Then, among the thus generated first filial generation plants, "SA3" and "SA7" which are capable of bearing seedless bell peppers as well as having a male sterile trait and a parthenocarpic trait are selected. Thereafter, these "SA3" and "SA7" are subjected to sequential backcrossing with a DH (Double Haploid) line (a fixed homozygous line) such as "Mi 74" which has been produced through anther culture of a bell pepper of a known parthenocarpic breeding line "Miogi (a cultivar available from Japan Horticultural Production and Research Institute)", as a pollen parent. By so doing, plants capable of bearing seedless bell peppers such as "3 Mi 74-2" plant and "3 Mi 74-4" plant can be generated. The "3 Mi 74-2" is generated by two backcross cycles of "SA3" with "Mi 74", and "3 Mi 74-4" is generated by four backcross cycles of "SA3" with "Mi 74". In addition, progeny plants capable of bearing seedless bell peppers can be stably generated by crossing the plants of "3 Mi 74-2" or "3 Mi 74-4" with pollen harvested from "Mi 74".

EXAMPLES

Next is a more detailed description of the present invention with reference to examples. However, the present invention is not to be limited to these examples. Each bell pepper was cultivated by a conventional method.

<Selection of First Filial Generation Plants Having Male Sterile Trait, Parthenocarpic Trait, and Seedless Fruit-Generating Property>

First, bell peppers of a known male sterile "MS Shosuke" were cultured in a plastic greenhouse in which natural pollination can be avoided.

The pistil of each cultured plant of "MS Shosuke" was respectively applied with pollen harvested from a known breeding line "A3" to effect cross, by which first filial generation plants were generated. Among these first filial generation plants, a first filial generation plant "SA3" capable of bearing seedless fruits as well as having a male sterile trait and a parthenocarpic trait, was selected. Other known breeding lines "A7", "A21", "A27", and "A33" were also respectively used instead of the breeding line "A3" to cross with the "MS Shosuke" line, by which first filial generation plants "SA7", "SA21", "SA27", and "SA33" capable of bearing seedless fruits as well as having a male sterile trait and a parthenocarpic trait were respectively selected.

<Production of Seedless Fruit-Generating Plant of the Present Invention>

First, for use as a pollen parental fixed line to be crossed with the selected first filial generation plants, a known breeding line "Miogi" was subjected to anther culture, and thereby six DH lines of "Mi 54", "Mi 64", "Mi 74", "Mi 144", "Mi 152", and "Mi 159" were produced. A known breeding line of "Tosahime R" was also subjected to anther culture in the same manner, and thereby six DH lines of "To 33", "To 55", "To 57", "To 71", "To 119", and "To 120" were produced. The "Miogi" line was cultivated from a seed obtained from Japan Horticultural Production and Research Institute, and the "Tosahime R" line was cultivated from a seed obtained from Kochi Prefectural Economic Federation.

Pollen was respectively harvested from the thus produced DH lines and crossed with five first filial generation plants of "SA3", "SA7", "SA21", "SA27", and "SA33", and thereby their seeds (progeny plants) were obtained. These seeds were cultivated and allowed to fructify themselves without fertilization. The fertility of the thus generated fruits was observed.

As a result, all progeny plants obtained by respective crossings between the six DH lines of "Tosahime R" and the five varieties of the first filial generation plants, carried seeds and thus were found to be not seedless fruit-generating plants.

On the other hand, the progeny plants obtained by respective crossings between the six DH lines of "Miogi" and the five varieties of the first filial generation plants, were investigated for the fertility, by which the results as shown in Table 1 were given. In the table, the symbol "○" represents a result in which the progeny plant was sterile, the symbol "x" represents a result in which the progeny plant was fertile, and the symbol "-" means no data available.

TABLE 1

| | Pollen parent | | | | | |
|---|---|---|---|---|---|---|
| | Mi 54 | Mi 64 | Mi 74 | Mi 144 | Mi 152 | Mi 159 |
| SA3 | ○ | ○ | ○ | — | ○ | ○ |
| SA7 | ○ | ○ | ○ | — | ○ | ○ |
| SA21 | x | — | x | — | x | — |
| SA27 | x | — | x | — | x | — |
| SA33 | x | x | x | x | x | x |

The "SA3" and "SA7" were found to be capable of bearing progeny plants having a parthenocarpic trait and a male sterile trait, when crossed with any one of the five lines of "Mi 54", "Mi 64", "Mi 74", "Mi 152", and "Mi 159", as a pollen parent. Moreover, progeny plants thereof were found to be seedless fruit-generating plants. Furthermore, these progeny plants were backcrossed with a plant of the DH line used as the pollen parent for the production, as a pollen parent, and thereby their seeds (progeny plants) were obtained. These seeds were cultivated and allowed fructify themselves without fertilization. The thus generated fruits were investigated. As a result, these progeny plants were found to be seedless fruit-generating plants having a parthenocarpic trait and a male sterile trait like their parents.

In particular, all progeny plants obtained by respective crossings between "SA3" and "Mi 54", "SA3" and "Mi 74", "SA3" and "Mi 152", "SA7" and "Mi 54", "SA7" and "Mi 64", and "SA7" and "Mi 152" were found to be seedless fruit-generating plants having a male sterile trait, as a result of backcrossing up to the third generation progeny plants. In addition, the quality such as the taste and the flavor as well as the yield of seedless bell peppers generated from these seedless fruit-generating plants were close to those of the "Miogi" bell peppers serving as the pollen parent, showing that these seedless fruit-generating plants had favorable properties as edible cultivation varieties. Among the obtained seedless fruit-generating plants, the progeny plant obtained by crossing between "SA3" and "Mi 74" was named "3 Mi 74". Furthermore, the "3 Mi 74" plant was subjected to sequentially repeating backcrossing with "Mi 74" as a pollen parent, and thereby their progeny plants were generated. These progeny plants were all seedless fruit-generating plants.

The thus obtained seedless fruit-generating plants and the pollen parental fixed lines thereof are novel plants created by the inventors of the present invention. Therefore, among these progeny plants, the inventors of the present invention deposited the seeds of "3 Mi 74-2" and "3 Mi 74-4", and the seed of their pollen parental fixed line "Mi 74" as novel plants, with International Patent Organism Depositary, National Institute of Advanced Industrial Science and Technology, which is located at AIST Tsukuba Central, 6, 1-1, Higashi 1-chome, Tsukuba-shi, Ibaraki-ken 305-8566, JAPAN. The accession numbers are FERM BP-10934 for "Mi 74", FERM BP-10935 for "3 Mi 74-2", and FERM BP-10936 for "3 Mi 74-4". The date of deposit was Nov. 28, 2007.

INDUSTRIAL APPLICABILITY

The seedless fruit-generating plant of the present invention and the variety produced by the production method of the present invention are capable of readily and reliably bearing seedless fruits by means of fructification rather than mere fertilization, and thus can be applied particularly to the field of cultivation of edible seed fruits.

The invention claimed is:

1. A method of producing a *Capsicum annuum* variety capable of bearing commercially acceptable seedless fruits stably over several generations by backcrossing, wherein a *C. annuum* plant of a male sterile variety having a genetically determined parthenocarpic trait is backcrossed with a recurrent *C. annuum* plant of a fixed homozygous parthenocarpic line which is capable of bearing commercially acceptable seedless fruits and sustaining the genetically determined parthenocarpic trait and the genetically determined male sterile trait of the *C. annuum* plant, wherein said fixed line is used as a pollen parent and wherein the male sterile *C. annuum* plant is backcrossed to said fixed homozygous line as the recurrent parent at least one time, to thereby produce a *C. annuum* variety bearing commercially acceptable seedless fruits stably over several generations.

2. The method of producing a *C. annuum* variety capable of bearing commercially acceptable seedless fruits stably over several generations by backcrossing according to claim 1, wherein said *C. annuum* variety is obtained by a crossing method comprising the following steps (a) and (b):

a step (a) of selecting a first filial generation plant which is capable of bearing seedless fruits as well as having a genetically determined male sterile trait and a genetically determined parthenocarpic trait from the group of first filial generation plants generated by crossing between a *C. annuum* pepper plant of a male sterile line and a *C. annuum* plant of a parthenocarpic line; and a step (b) of backcrossing the thus selected first filial generation *C. annuum* plant with a *C. annuum* plant of a fixed homozygous parthenocarpic line which is capable of bearing commercially acceptable seedless fruits and sustaining the genetically determined parthenocarpic trait and the genetically determined male sterile trait of the selected first filial generation plant, wherein said fixed homozygous line is used as a pollen parent, to thereby generate a progeny *C. annuum* plant having the genetically determined parthenocarpic trait and the genetically determined male sterile trait and bearing commercially acceptable seedless fruits stably over several generations.

3. The method of producing a *C. annuum* variety capable of bearing commercially acceptable seedless fruits stably over several generations by backcrossing according to claim 1, wherein said *C. annuum* variety is obtained by a crossing method comprising the following steps (a) to (c) while repeating the step (c) at least one time:

a step (a) of selecting a first filial generation *C. annuum* plant which is capable of bearing seedless fruits as well as having a genetically determined male sterile trait and a genetically determined parthenocarpic trait from the group of first filial generation plants generated by crossing between a plant of a *C. annuum* male sterile line and a *C. annuum* plant of a parthenocarpic line;

a step (b) of crossing the thus selected first filial generation plant with a *C. annuum* plant of a fixed homozygous parthenocarpic line which is capable of bearing commercially acceptable seedless fruits and sustaining the genetically determined parthenocarpic trait and the genetically determined male sterile trait of the selected first filial generation plant, wherein said fixed line is used as a pollen parent, to thereby generate a progeny *C. annuum* plant having the genetically determined parthenocarpic trait and the genetically determined male sterile trait; and a step (c) of backcrossing the thus generated progeny plant again with a *C. annuum* plant of the fixed homozygous parthenocarpic line used as the pollen parent in the step (b), wherein said fixed line is also used as a pollen parent, to thereby generate a progeny *C. annuum* plant having the genetically determined parthenocarpic trait and the genetically determined male sterile trait and bearing commercially acceptable seedless fruits stably over several generations.

4. The method of producing a *C. annuum* variety capable of bearing commercially acceptable seedless fruits stably over several generations by backcrossing according to claim 1, wherein said fixed homozygous parthenocarpic line is a line fixed through anther culture or ovule culture.

5. The method of producing a *C. annuum* variety capable of bearing commercially acceptable seedless fruits stably over several generations by backcrossing according to claim 1, wherein said variety capable of bearing commercially acceptable seedless fruits stably over several generations is a bell pepper.

6. The method of producing a *C. annuum* variety capable of bearing commercially acceptable seedless fruits stably over several generations by backcrossing according to claim 5, wherein said *C. annuum* variety is selected from the group consisting of 3 Mi 74-2 (FERM BP-10935), 3 Mi 74-4 (FERM BP-10936), and a progeny *C. annuum* plant of any of the preceding deposited plants;

wherein said progeny plant has the genetically determined parthenocarpic trait and the genetically determined male sterility trait and is capable of bearing commercially acceptable seedless fruits stably over several generations.

7. The method of producing a *C. annuum* variety capable of bearing commercially acceptable seedless fruits stably over several generations by backcrossing according to claim 5, wherein said fixed line is Mi 74 (FERM BP-10934).

8. A *C. annuum* variety capable of bearing commercially acceptable seedless fruits stably over several generations produced according to the method of claim 1.

9. A commercially acceptable seedless fruit generated from a *C. annuum* plant of said variety according to claim 8 by means of fructification rather than fertilization.

* * * * *